United States Patent [19]

Swidersky et al.

[11] Patent Number: 5,679,613
[45] Date of Patent: Oct. 21, 1997

[54] CHLOROFLUORO(HYDRO)CARBON CONVERSION PROCESS

[75] Inventors: Hans-Walter Swidersky, Hanover; Johannes Eicher, Garbsen; Thomas Born, Holle; Carsten Brosch, Seelze; Werner Rudolph, Hanover, all of Germany

[73] Assignee: Solvay Fluor und Derivate GmbH, Hanover, Germany

[21] Appl. No.: 414,236

[22] Filed: Mar. 31, 1995

Related U.S. Application Data

[62] Division of Ser. No. 323,015, Oct. 14, 1994, Pat. No. 5,430,201.

[30] Foreign Application Priority Data

| Oct. 15, 1993 | [DE] | Germany | 43 35 178.6 |
| Dec. 11, 1993 | [DE] | Germany | 43 42 330.2 |

[51] Int. Cl.$^6$ .............. B01J 27/125; B01J 27/06; B01J 27/128
[52] U.S. Cl. .............. 502/231; 502/224; 502/229
[58] Field of Search .............. 502/231, 224, 502/229; 423/463, 465, 489, 490

[56] References Cited

U.S. PATENT DOCUMENTS

| 2,598,411 | 5/1952 | Miller et al. | 260/653 |
| 3,087,974 | 4/1963 | Hauptschein et al. | 260/653 |
| 4,570,023 | 2/1986 | Petruck et al. | 570/210 |
| 4,599,441 | 7/1986 | Kanner et al. | 556/469 |

FOREIGN PATENT DOCUMENTS

| 404297 | 12/1990 | European Pat. Off. . |
| 1453510 | 9/1966 | France . |
| 1668346 | 4/1971 | Germany . |
| 3013888 | 10/1981 | Germany . |
| 40-28567 | 12/1965 | Japan . |
| J5 6099-429 | 1/1980 | Japan . |
| JO1172-347-A | 12/1987 | Japan . |
| WO 91/05753 | 5/1991 | WIPO . |

OTHER PUBLICATIONS

Okuhara, *J. Org. Chem.*, vol. 43, No. 14, pp. 2745–2749 (1978).

Hellberg et al., *Chemiker–Zeitung* (Chemist Magainze), vol. 93, No. 6, pp. 209–211 (1969) no English version.

*Primary Examiner*—Glenn A. Caldarola
*Assistant Examiner*—Thuan D. Dang
*Attorney, Agent, or Firm*—Evenson, McKeown, Edwards & Lenahan P.L.L.C.

[57] ABSTRACT

A process for preparing R113a from R113, and R123 from R123a or R123b by rearrangement over $AlCl_3$, in which when the reaction mixture is heated sudden start-up of the reaction, which often causes large amounts of heat to be released and the reaction to run away, is prevented by using a specially activated $AlCl_3$, which has been activated by means of a metal halide selected from the group consisting of $NaF \cdot nHF$ with $0 < n \leq 2$, AgCl and $FeCl_3$. In addition to it being considerably easier to control the reaction, shorter reaction times for the rearrangement and a decrease in the amount of by-products which are formed, are observed.

8 Claims, No Drawings

CHLOROFLUORO(HYDRO)CARBON CONVERSION PROCESS

This application is a division of my application Ser. No. 08/323,015, filed Oct. 14, 1994 now U.S. Pat. No. 5,430,203.

BACKGROUND OF THE INVENTION

This invention relates to a process for preparing compounds corresponding to the formula (I) $CF_3CCl_2X$, wherein X=Cl or H, by rearrangement using an $AlCl_3$ catalyst.

$CF_3CCl_3$ is a starting material for chemical synthesis. For example, it can be reacted with $SO_3$ to give trifluoroacetyl chloride, which in turn is used in chemical synthesis. By hydrogenating $CF_3CCl_3$ (R113a), chlorofluorohydrocarbons can be prepared which are used as substitutes for fully halogenated carbon compounds, as solvents or propellants. $CF_3CHCl_2$ is such a solvent or propellant. It is already known that, for example, $CF_3CCl_3$ can be prepared by rearrangement of $CF_2ClCFCl_2$ over aluminum chloride. A drawback of this reaction is that it starts up only at elevated temperature, but then takes place with large amounts of heat being released, so that the batch is often observed to run away.

SUMMARY OF THE INVENTION

It is an object of the present invention is to provide a process for preparing $CF_3CCl_3$ and $CF_3CHCl_2$ by rearrangement over aluminum chloride, which can be carried out with shortened reaction times.

Another object of the invention is to provide a process for preparing $CF_3CCl_3$ and $CF_3CHCl_2$ by rearrangement over aluminum chloride, which can be carried out with reduced formation of by-products.

It is also an object of the invention to provide a process for preparing $CF_3CCl_3$ and $CF_3CHCl_2$ by rearrangement over aluminum chloride, in which there is a reduced tendency for the reaction to run away.

A further object of the invention is to provide an improved catalyst for preparing $CF_3CCl_3$ and $CF_3CHCl_2$ by rearrangement.

These and other objects of the invention are achieved by providing a process for preparing a compound corresponding to the formula $CF_3CCl_2X$, where X represents Cl or H, comprising subjecting $CF_2ClCFCl_2$, if X=Cl, or subjecting $CF_2ClCHClF$ or $CF_2HCCl_2F$, if X=H, to catalytic rearrangement in the presence of an $AlCl_3$ catalyst, wherein the $AlCl_3$ catalyst is $AlCl_3$ which has been activated by a metal halide selected from the group consisting of AgCl, $FeCl_3$ and acid salts corresponding to the formula $NaF \cdot nHF$, where $0 < n \leq 2$.

In accordance with a further aspect of the invention, the objects are achieved by providing an aluminum chloride rearrangement catalyst obtained by contacting $AlCl_3$ and a metal halide selected from the group consisting of AgCl, $FeCl_3$ and salts corresponding to the formula $NaF \cdot nHF$, wherein $0 < n \leq 2$, with the proviso that if said metal halide is $FeCl_3$, sufficient $FeCl_3$ is present to give an Fe content of at least 40 ppm.

DETAILED DESCRIPTION OF THE PREFERRED EMBODIMENTS

The process according to the invention for preparing compounds of the formula (I) $CF_3CCl_2X$ wherein X=Cl or H, by rearrangement of $CF_2ClCFCl_2$, if X=Cl, or by rearrangement of $CF_2ClCHClF$ or $CF_2HCCl_2F$, if X=H, over $AlCl_3$ as the catalyst, is characterized in that the catalyst employed is $AlCl_3$ which has been activated by means of a metal halide selected from the group consisting of AgCl, $FeCl_3$ and acid salts of the formula (II) $NaF \cdot nHF$ wherein $0 < n \leq 2$. The activation in this context is carried out with substantially anhydrous compounds.

In accordance with one preferred embodiment, $CF_3CCl_3$ is prepared from $CF_2ClCFCl_2$. The invention will be described in further detail hereinafter with reference to such preferred embodiment as an example.

It is possible to employ pure $CF_2ClCFCl_2$. However, is preferred to employ this starting compound in the form of a mixture of $CF_2ClCFCl_2$ and $CF_3CCl_3$, as produced in industrial processes.

When a salt of the formula (II) is used to activate the catalyst, the parameter n is preferably greater than 0.5 and less than or equal to 2. It will be apparent to persons skilled in the art that, if mixtures in which n<1 are present, they are actually mixtures of NaF together with HF adducts of NaF. Preferably, compounds of the formula (II) are used whose composition is within the range whose limits are represented by the formulas $NaF \cdot 0.8\ HF$ and $NaF \cdot 1.5\ HF$. The preferred compound of the formula (II) is $NaF \cdot HF$ (i.e. n=1).

The rearrangement is preferably carried out at a temperature between 70° and 95° C. Alternatively, the rearrangement can be carried out at lower temperatures, in which case, the degree of conversion may be lower. Alternatively, the rearrangement can be carried out at higher temperatures, but this may result in increased formation of by-products. Because of the beginning exothermic reaction, it is advisable to heat the reaction mixture slowly at first, to temperatures in the range of from 70° to 80° C. and, if the exothermic reaction begins, to adjust the heating output accordingly or even provide for cooling in order to achieve operation in the particularly preferred range of from 75° to 90° C.

Advantageously, the metal halide content of the activated catalyst is at least 40 ppm of Fe, Ag or Na in the form of $FeCl_3$, AgCl or $NaF \cdot nHF$. Particularly good results in terms of selectivity and reaction rate in the rearrangement are achieved if the activating metal halide, e.g. acid salt of the formula (II), and $AlCl_3$ are used in a weight ratio of between 1:5 and 1:100, especially between 1:10 and 1:100. The activated catalyst is preferably present in the reaction mixture in an amount of from 0.1 to 10% by weight [total weight of the $AlCl_3$ and the activating metal halide, e.g. the salt of formula (II)].

The rearrangement according to the invention can be carried out at atmospheric pressure or, if desired, at reduced or elevated pressure, e.g. up to 5 bar (abs).

The invention further relates to a rearrangement catalyst composed of aluminum chloride, which catalyses the rearrangement of chlorofluoro(hydro)carbons, which catalyst can be obtained by contacting $AlCl_3$ and a metal halide selected from the group consisting of AgCl, FeCl and acid salts of the formula (II). A preferred rearrangement catalyst can be obtained by contacting $AlCl_3$ and AgCl, $FeCl_3$ or a salt of the formula $NaF \cdot nHF$, wherein $0.5 < n \leq 2$, especially in $CF_2ClCCl_2F$. As used herein, the term "contacting" refers to mixing the $AlCl_3$ and the metal halide, preferably in $CF_2ClCCl_2F$. Particularly effective rearrangement catalysts are obtained in the process if the contacting of the $AlCl_3$ and the metal halide, especially AgCl, $FeCl_3$ or $NaF \cdot HF$, is carried out in $CF_2ClCCl_2F$ for a duration of at least 1 hour, preferably for a duration between 3 and 10 hours. The weight ratio between the $AlCl_3$ and the metal halide is preferably in the range between 5:1 and 100:1. If desired, the solvent can then be removed, e.g. by evaporation or filtration.

The invention further relates to aluminum chloride rearrangement catalysts characterized by a content of a metal halide selected from the group consisting of AgCl, FeCl$_3$ and acid salts of the formula (II) with the proviso that aluminum chloride with a content of up to 40 ppm of Fe in the form of FeCl$_3$ is excluded. Commercially available aluminum trichloride AR contains up to 40 ppm of Fe in the form of FeCl$_3$ and is not claimed. Preferred catalysts contain more than 40 ppm, up to 10% by wt especially from 70 to 150 ppm of Fe, Ag or Na in the form of FeCl$_3$, AgCl or NaF·nHF.

The preparation of the last-mentioned aluminum chloride rearrangement catalyst is achieved, for example, by mixing the constituents mentioned in the desired weight ratio, or with the desired weight ratio or the desired catalyst composition being formed, or by starting from silver- and/or iron-containing aluminum compounds and converting the mixture into the corresponding chlorides.

The rearrangement catalysts obtained according to the above-described processes are suitable for use in the conversion process according to the invention. In this context, the preferred rearrangement catalysts are distinguished by especially high catalytic activity in the rearrangement.

The process according to the invention may be advantageously carried out as follows: first a premix (which likewise is part of the invention) is produced of the rearrangement catalyst which consists of from 0.1 to 200 parts by weight of AlCl$_3$, as finely dispersed as possible, and from 0.01 to 1 part by weight of the metal halide, e.g. of the salt of formula (II), especially NaF·HF (likewise as finely dispersed as possible), and from 0 to 99.89 parts by weight of CF$_2$ClCCl$_2$F. Optimally, a suspension of the solids in CF$_2$ClCCl$_2$F is produced with a solids content between 0.1 and 10% by weight. This premix of the rearrangement catalyst is preferably allowed to remain in contact for at least 1 hour, especially up to 10 hours, at a temperature from 10° to 30° C., preferably at ambient temperature. At the same time, the mixture should preferably be stirred. After the contact time has ended, the premix, which has transmuted into the rearrangement catalyst according to the invention, is added to the comoound to be rearranged (or to the mixture which contains the compound to be rearranged). The mixture is then heated.

Alternatively, the starting point is aluminum chloride which, as a result of the manner in which it is prepared, contains the desired amount of silver chloride or iron chloride, or in which, during the preparation, the aluminum starting compounds have been admixed with silver or silver compounds, or iron compounds or iron, respectively.

The degree of conversion in carrying out the process can be monitored by conventional analysis methods, for example gas chromatography. After the rearrangement is complete, volatile constituents are evaporated and separated in a conventional manner, for example by distillation. The rearrangement catalyst can be reused.

First of all, the process according to the invention has the advantage that shorter reaction times are possible. In conventional processes without activation of the catalyst, distinct delays are possible at the start of the reaction, so that the reaction often runs away. ControLling the reaction conditions is easier in the process according to the invention. Moreover, less by-products are produced.

The invention is illustrated in further detail by the following examples, without limiting its scope.

Example 1

Preparation of the premix of the conversion catalyst, and preparation of the conversion catalyst.
1.1. Without extending the contact time.
1.1.1. Weight ratio of AlCl$_3$ to NaF·HF 10:1.

30 g of AlCl$_3$ powder (from BASF) and 3 g of NaF·HF (likewise in the form of a powder) were mixed together with the addition of 300 g of pure R113 (CF$_2$ClCFCl$_2$). The mixture was employed immediately for the conversion of the R113 added.

1.1.2. Weight ratio between AlCl$_3$ and NaF·HF 6.7:1.

Example 1.1.1. was repeated, except that this time 20 g of AlCl$_3$ powder were mixed with 3 g of NaF·HF with the addition of 300 g of a mixture of the isomers CF$_2$ClCFCl$_2$ and CF$_3$CCl$_3$ (R113/R113a) in a weight ratio of 10.3:89.7. This mixture was also used at once for converting the R113.
1.2. Preparation of the rearrangement catalyst with extension of the contact time.
1.2.1. Contact time of 1.5 hours.

30 g of aluminum chloride powder and 3 g of NaF·HF were brought into contact for 1.5 hours in 300 g of an isomer mixture of R113 and R113a in a weight ratio of 12.6:87.4.

1.2.2. Extension of the contact time to 5 hours 30 g of aluminum chloride powder and 3 g of NaF·HF were brought into contact at room temperature for 5 hours in 300 g of an isomer mixture of R113 and R113a in a weight ratio of 10.3:89.7.

Example 2

Carrying out of the conversion reaction.
2.1. Execution using the catalyst prepared in accordance with Example 1.1.1.

The mixture of aluminum chloride, NaF·HF and R113, prepared in accordance with Example 1.1.1., was heated until the reaction started up (temperature of 79° C.). The mixture was then stirred for 20 minutes at a temperature of not more than 108° C. Volatile constituents were evaporated. The ratio of the isomers 113 and 113a was 0.1:99.9. The sum of the by-products was 15.8%.
2.2. Carrying out using the catalyst prepared in accordance with Example 1.1.2.

The mixture of aluminum chloride, NaF·HF and the isomer mixture R113/R113a was heated until the reaction started up (approximately 77° C.). The mixture was then held at a temperature of no more than 81° C. for 30 minutes. The initial isomer ratio R113/R113a of 10.3:89.7 had shifted to a ratio of 1.2:98.8. The sum of the by-products was 7.9%.
2.3. Carrying out the conversion with an isomer mixture R113/R113a in a ratio of 10.3:89.7.

30 g of aluminum chloride powder, 3 g of NaF·HF and 300 g of an isomer mixture of R113 and R113a in a ratio of 10.3:89.7 were heated, without extending the activation time, i.e. immediately after mixing, until the reaction started up (approximately 82° C.). The mixture was then maintained for 10 minutes at a temperature of no more than 88° C. The final concentration of the isomer mixture of R113/R113a was 0.03:99.97. The sum of the by-products was 11.6% by weight.
2.4. Carrying out the conversion using the catalyst prepared in accordance with Example 1.2.1.

The mixture, prepared in accordance with Example 1.2.1., of aluminum chloride, NaF·HF and the isomer mixture of R113 and R113a, having been stirred for 1.5 hours at room temperature, was heated until the reaction started up (at approximately 80° C.). The mixture was then maintained for 30 minutes at a temperature of no more than 85° C. The final concentration of the isomer mixture of R113/R113a was 0.03:99.97. The sum of the by-products was 13.8% by weight.

2.5. Carrying out the conversion using the catalyst, activated for 5 hours, from Example 1.2.2.

The mixture of aluminum chloride, NaF·HF and the isomer mixture of R113/R113a, whose preparation was described in Example 1.2.2., was stirred for 5 hours at room temperature. The mixture was then heated until the reaction started up (approximately 77° C.). It was then maintained for 30 minutes at a temperature of no more than 79.5° C. The initial isomer ratio of R113 to R113a of 10.3:89.7 had shifted to a ratio of 0.05:99.95. The sum of the by-products was 11.4% by weight.

As the examples show, a rearrangement catalyst produced by extending the contact time is particularly effective. This manifests itself in a very high degree of conversion being achieved even at a relatively low reaction temperature.

Example 3

Use of aluminum chloride containing iron trichloride as the rearrangement catalyst.

Aluminum chloride was employed to which $FeCl_3$ had been added until 74 ppm of Fe were present.

In a reactor, 15.04 kg of R113 were introduced as the initial charge and heated to approximately 75° C. 100 g of the $AlCl_3$ which, due to its preparation, contained iron trichloride, were added, whereupon a strongly exothermic reaction began (heating up to 116.6° C.). After the exothermic reaction was complete, the reaction mixture was stirred for approximately 40 minutes at a temperature of 100° C. After a sample for gas chromatography (GC) analysis was taken, the heater was turned off, and the reaction mixture was stirred for a further 4 hours. Further samples were taken 2 hours and 4 hours after the heating had been switched off.

The analysis results are tabulated below:

GC analysis of the sample taken after 1 hr (data in area %):

| | |
|---|---|
| Content of compounds having the empirical formula | $C_2Cl_3F_3$:89.02 |
| Content of compounds having the empirical formula | $C_2Cl_2F_4$:2.95 |
| Content of compounds having the empirical formula | $C_2Cl_4F_2$:5.94 |
| Content of compounds having the empirical formula | $C_2Cl_6$:1.21 |
| Content of compounds having the empirical formula | $C_2Cl_5F$:0.83 |

Isomer distribution of the compounds of the formula $C_2Cl_3F_3$:

R113a:99.53

R113:0.47

GC analysis of the sample taken after 3 hr (data in area %):

| | |
|---|---|
| Content of compounds having the empirical formula | $C_2Cl_3F_3$:89.04 |
| Content of | $C_2Cl_2F_4$:2.31 |
| compounds having the empirical formula | |
| Content of compounds having the empirical formula | $C_2Cl_4F_2$:4.14 |
| Content of compounds having the empirical formula | $C_2Cl_6$:3.23 |
| Content of compounds having the empirical formula | $C_2Cl_5F$:1.26 |

Isomer distribution of the compounds of the formula $C_2Cl_3F_3$:

R113a:99.73

R113:0.27

GC analysis of the sample taken after 5 hr (data in area %):

| | |
|---|---|
| Content of compounds having the empirical formula | $C_2Cl_3F_3$:87.77 |
| Content of compounds having the empirical formula | $C_2Cl_2F_4$:2.8 |
| Content of compounds having the empirical formula | $C_2Cl_4F_2$:4.21 |
| Content of compounds having the empirical formula | $C_2Cl_6$:3.46 |
| Content of compounds having the empirical formula | $C_2Cl_5F$:1.37 |

Isomer distribution of the compounds of the formula $C_2Cl_3F_3$:

R113a:99.75

R113:0.25

Conclusion: After as little as one hour, the R113 employed was virtually completely reacted to give the isomer R113a, with only insignificant amounts of by-product being formed.

Example 4

Preparation and use of an aluminum trichloride activated with AgCl.

In a 300 $cm^3$ autoclave made of alloy steel and equipped with temperature sensors for measuring the internal temperature, and with a manometer, 300 g of a 113/113a mixture (weight ratio 10.3:89.7) were admixed with 33 g of a conversion catalyst prepared by mixing 30 g of aluminum trichloride powder (supplier: Riedel de Haan) and 3 g of AgCl powder. With stirring, heating to 91° C. took place over the course of 15 minutes. The product obtained after the reaction was complete contained, according to gas-chromatographic analysis, 87.3 area % of 113a (isomeric purity: 100%) and a total sum of 12.7 area % of minor components (114a, 112a, 111 and 110).

As can be seen from this example, the aluminum trichloride activated with silver chloride is particularly advantageous as a rearrangement catalyst.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An aluminum chloride rearrangement catalyst obtained by contacting $AlCl_3$ and a metal halide selected from the group consisting of AgCl and salts corresponding to the formula (II):

$$NaF \cdot nHF \qquad (II)$$

wherein $0 < n \leq 2$; said catalyst having a content of Ag or Na in the range of from more than 40 to 10,000 ppm.

2. A rearrangement catalyst according to claim 1, obtained by contacting $AlCl_3$ and AgCl.

3. A rearrangement catalyst according to claim 1, obtained by contacting $AlCl_3$ and a salt corresponding to the formula $NaF \cdot nHF$, wherein $0 < n \leq 2$, in $CF_2ClCCl_2F$.

4. A rearrangement catalyst according to claim 3 obtained by contacting $AlCl_3$ and $NaF \cdot HF$ in $CF_2ClCCl_2F$ for a period of at least one hour.

5. An aluminum chloride rearrangement catalyst containing a metal halide selected from the group consisting of AgCl and acid salts of the formula (II)

$$NaF \cdot nHF \qquad (II)$$

wherein $0 < n \leq 2$, with a content of Ag or Na in the range of from more than 40 to 10,000 ppm, in the form of AgCl or $NaF \cdot nHF$.

6. An aluminum chloride rearrangement catalyst according to claim 5, containing from 70 to 150 ppm of Ag, or Na.

7. A catalyst premix consisting of 0.1 to 200 parts by weight of powdered $AlCl_3$, 0.01 parts by weight of a powdered metal halide selected form the group consisting of AgCl and $NaF \cdot nMF$, where $0 < n \leq 2$, and 0 to 99.89 parts of $CF_2ClCCl_2F$.

8. A catalyst premix comprising:
   0.1 to 10% by weight of a solids mixture consisting of 0.1 to 200 parts by weight of powdered $AlCl_3$, 0.01 parts by weight of powdered $FeCl_3$; and
   the balance to 100% by weight of $CF_2ClCCl_2F$.

* * * * *